United States Patent
Cazares et al.

(10) Patent No.: US 7,653,431 B2
(45) Date of Patent: Jan. 26, 2010

(54) ARRHYTHMIA DISCRIMINATION BASED ON DETERMINATION OF RATE DEPENDENCY

(75) Inventors: Shelley Cazares, Minneapolis, MN (US); Jaeho Kim, Redmond, WA (US); Yayun Lin, St. Paul, MN (US); Carlos Ricci, Apple Valley, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 532 days.

(21) Appl. No.: 11/312,280

(22) Filed: Dec. 20, 2005

(65) Prior Publication Data

US 2007/0142737 A1   Jun. 21, 2007

(51) Int. Cl.
*A61B 5/04* (2006.01)
(52) U.S. Cl. ...................................... 600/515
(58) Field of Classification Search ........................ None
See application file for complete search history.

(56) References Cited

U.S. PATENT DOCUMENTS

| | | | |
|---|---|---|---|
| 4,023,564 A | 5/1977 | Valiquette et al. |
| 4,336,810 A | 6/1982 | Anderson et al. |
| 4,428,378 A | 1/1984 | Anderson et al. |
| 4,550,221 A | 10/1985 | Mabusth |
| 4,686,332 A | 8/1987 | Greanias et al. |
| 4,865,036 A | 9/1989 | Chirife |
| 4,872,459 A | 10/1989 | Pless et al. |
| 4,880,005 A | 11/1989 | Pless et al. |
| 5,144,947 A | 9/1992 | Wilson |
| 5,161,527 A | 11/1992 | Nappholz et al. |
| 5,176,137 A | 1/1993 | Erickson et al. |
| 5,217,021 A | 6/1993 | Steinhaus et al. |
| 5,257,621 A | 11/1993 | Bardy et al. |
| 5,312,445 A | 5/1994 | Nappholz et al. |
| 5,330,505 A | 7/1994 | Cohen |
| 5,330,508 A | 7/1994 | Gunderson |
| 5,411,031 A * | 5/1995 | Yomtov ..................... 600/519 |
| 5,447,519 A | 9/1995 | Peterson |
| 5,458,620 A | 10/1995 | Adams et al. |
| 5,554,177 A | 9/1996 | Kieval |

(Continued)

FOREIGN PATENT DOCUMENTS

EP   0547733   6/1993

(Continued)

OTHER PUBLICATIONS

U.S. Appl. No. 11/151,102.

(Continued)

*Primary Examiner*—George R Evanisko
*Assistant Examiner*—Andrew Hayes
(74) *Attorney, Agent, or Firm*—Hollingsworth & Funk, LLC

(57) ABSTRACT

Cardiac systems and methods provide for discriminating between supraventricular tachyarrhythmia and ventricular tachyarrhythmia based on a determination that the patient's supraventricular rhythm exhibits rate dependency. One approach involves determining if a patient's supraventricular rhythm exhibits rate dependent morphology. If the patient's supraventricular rhythm is determined to exhibit rate dependent morphology, an implantable device classifies a detected tachyarrhythmia episode based on one or more templates selected from a plurality of rate-indexed templates stored in the device. Determining if the supraventricular rhythm exhibits rate dependent morphology may also include determining one or more rates at which the rate dependent morphology occurs.

12 Claims, 10 Drawing Sheets

U.S. PATENT DOCUMENTS

| | | | |
|---|---|---|---|
| 5,587,977 | A | 12/1996 | Murata |
| 5,725,559 | A | 3/1998 | Alt et al. |
| 5,779,645 | A | 7/1998 | Olson et al. |
| 5,782,888 | A | 7/1998 | Olson et al. |
| 5,817,027 | A | 10/1998 | Arand et al. |
| 5,844,506 | A | 12/1998 | Binstead |
| 5,846,263 | A | 12/1998 | Peterson et al. |
| 5,857,977 | A | 1/1999 | Caswell et al. |
| 5,978,707 | A | 11/1999 | Krig et al. |
| 6,076,014 | A | 6/2000 | Alt |
| 6,084,253 | A | 7/2000 | Turner, Jr. |
| 6,147,680 | A | 11/2000 | Tareev |
| 6,178,350 | B1 | 1/2001 | Olson et al. |
| 6,192,273 | B1 | 2/2001 | Igel et al. |
| 6,221,011 | B1 | 4/2001 | Bardy |
| 6,223,078 | B1 | 4/2001 | Marcovecchio |
| 6,230,055 | B1 | 5/2001 | Sun et al. |
| 6,253,102 | B1 | 6/2001 | Hsu et al. |
| 6,266,554 | B1 | 7/2001 | Hsu et al. |
| 6,270,457 | B1 | 8/2001 | Bardy |
| 6,275,732 | B1 | 8/2001 | Hsu et al. |
| 6,277,072 | B1 | 8/2001 | Bardy |
| 6,280,380 | B1 | 8/2001 | Bardy |
| 6,308,095 | B1 | 10/2001 | Hsu et al. |
| 6,312,378 | B1 | 11/2001 | Bardy |
| 6,336,903 | B1 | 1/2002 | Bardy |
| 6,358,203 | B2 | 3/2002 | Bardy |
| 6,368,284 | B1 | 4/2002 | Bardy |
| 6,393,316 | B1 | 5/2002 | Gillberg et al. |
| 6,398,728 | B1 | 6/2002 | Bardy |
| 6,400,986 | B1 | 6/2002 | Sun |
| 6,418,340 | B1 | 7/2002 | Conley et al. |
| 6,434,417 | B1 | 8/2002 | Lovett |
| 6,438,407 | B1 | 8/2002 | Ousdigian et al. |
| 6,438,410 | B2 | 8/2002 | Hsu et al. |
| 6,440,066 | B1 | 8/2002 | Bardy |
| 6,445,949 | B1 | 9/2002 | Kroll |
| 6,449,503 | B1 | 9/2002 | Hsu et al. |
| 6,480,734 | B1 | 11/2002 | Zhang et al. |
| 6,487,443 | B2 | 11/2002 | Olson et al. |
| 6,564,106 | B2 | 5/2003 | Guck et al. |
| 6,594,523 | B1 | 7/2003 | Levine |
| 6,611,713 | B2 | 8/2003 | Schauerte |
| 6,631,290 | B1 | 10/2003 | Guck et al. |
| 6,654,639 | B1 | 11/2003 | Lu |
| 6,684,100 | B1 | 1/2004 | Sweeney |
| 6,708,058 | B2 | 3/2004 | Kim et al. |
| 6,766,194 | B1 | 7/2004 | Kroll |
| 6,801,806 | B2 | 10/2004 | Sun et al. |
| 6,888,538 | B2 | 5/2005 | Ely et al. |
| 6,889,079 | B2 | 5/2005 | Bocek et al. |
| 6,909,916 | B2 | 6/2005 | Spinelli |
| 6,922,585 | B2 | 7/2005 | Zhou |
| 6,993,385 | B1 | 1/2006 | Routh |
| 7,031,764 | B2 | 4/2006 | Schwartz et al. |
| 7,076,289 | B2 | 7/2006 | Sakar et al. |
| 7,085,599 | B2 | 8/2006 | Kim et al. |
| 7,103,405 | B2 | 9/2006 | Sakar et al. |
| 7,107,098 | B2 | 9/2006 | Sharma et al. |
| 7,130,677 | B2 | 10/2006 | Brown et al. |
| 7,184,815 | B2 | 2/2007 | Kim et al. |
| 7,277,747 | B2 * | 10/2007 | Cazares et al. ............. 600/518 |
| 2002/0183637 | A1 | 12/2002 | Kim et al. |
| 2003/0045908 | A1 * | 3/2003 | Condie et al. ................. 607/9 |
| 2003/0120316 | A1 | 6/2003 | Spinelli et al. |
| 2003/0191403 | A1 | 10/2003 | Zhou et al. |
| 2003/0195572 | A1 * | 10/2003 | Bocek et al. .................. 607/9 |
| 2004/0093035 | A1 * | 5/2004 | Schwartz et al. .............. 607/5 |
| 2004/0111119 | A1 | 6/2004 | Sarkar |
| 2004/0111120 | A1 | 6/2004 | Sarkar |
| 2004/0111121 | A1 | 6/2004 | Brown |
| 2004/0167579 | A1 | 8/2004 | Sharma et al. |
| 2004/0176694 | A1 | 9/2004 | Kim et al. |
| 2004/0215092 | A1 * | 10/2004 | Fischell et al. .............. 600/515 |
| 2004/0215270 | A1 | 10/2004 | Ritscher et al. |
| 2004/0239650 | A1 | 12/2004 | Mackey |
| 2005/0131476 | A1 | 6/2005 | Kim et al. |
| 2005/0137485 | A1 | 6/2005 | Cao |
| 2005/0137641 | A1 | 6/2005 | Naughton |
| 2005/0192506 | A1 * | 9/2005 | Kim et al. ................... 600/510 |
| 2005/0288600 | A1 | 12/2005 | Zhang et al. |
| 2006/0069322 | A1 | 3/2006 | Zhang et al. |
| 2006/0074331 | A1 | 4/2006 | Kim et al. |
| 2006/0111643 | A1 * | 5/2006 | Cazares et al. .............. 600/518 |
| 2006/0111747 | A1 * | 5/2006 | Cazares et al. ................ 607/4 |
| 2006/0111751 | A1 | 5/2006 | Cazares |
| 2006/0253044 | A1 | 11/2006 | Zhang et al. |
| 2006/0281998 | A1 * | 12/2006 | Li ............................. 600/516 |

FOREIGN PATENT DOCUMENTS

| | | |
|---|---|---|
| EP | 0360412 | 3/1995 |
| EP | 0450943 | 1/1996 |
| EP | 0801960 | 9/2003 |
| EP | 1267993 | 1/2005 |
| EP | 1112755 | 9/2005 |
| WO | WO 02/24276 | 3/2002 |
| WO | 03047690 | 12/2003 |
| WO | WO 2006/039694 | 4/2006 |

OTHER PUBLICATIONS

U.S. Appl. No. 11/038,996.
U.S. Appl. No. 10/955,831, filed Sep. 30, 2004, Kim et al.
U.S. Appl. No. 11/312,279, filed Dec. 20, 2005, Cazares et al.
U.S. Appl. No. 10/995,655, filed Nov. 23, 2004, Cazares.
U.S. Appl. No. 11/209,976, filed Aug. 23, 2005, Li et al.
U.S. Appl. No. 10/995,704, filed Nov. 23, 2005, Cazares et al.
U.S. Appl. No. 11/089,185, filed Mar. 24, 2005, Kim et al.
"Vitality 2 Implantable Cardioverter Defibrillator System Guide", Guidant Corporation, 2004, Cover pages and pp. 3-15-3-19.
Gold, Michael R., et al., "Advanced Rhythm Discrimination for Implantable Cardioverter Defibrillators Using Electrogram Vector Timing and Correlation", *Journal of Cardiovascular Electrophysiology*, vol. 13, No. 11, Nov. 2002, pp. 1092-1097.
M. S. Wathen, M.D. et al. Shock Reduction Using Antitachycardia Pacing for Spontaneous Rapid Ventricular Tachycardia in Patients with Coronary Artery Disease. *Circulation 2001* vol. 104:796-801. © 2001 American Heart Association, Inc.
Martha Kerr. Shock Rate Cut 70% with ICDs Programmed to First Deliver Antitachycardia Pacing: Results of the PainFREE Rx II Trial. *NewsRhythms*. MedScape CRM News 2003. www.medscape.com.
Lake et al., *Am. J. Physiol. Regul. Integr. Comp. Physiol.*, 283: R789-97 (2002).
Richman et al., *Am. J. Physiol. Heart Circ. Physiol.*, 278: H2039-49 (2000).
Dubin, Rapid Interpretation of EKG's, 2000, Cover Publishing Company, 6th edition, p. 3334-345.

* cited by examiner

ARRHYTHMIA DISCRIMINATION BASED ON DETERMINATION OF RATE DEPENDENCY

FIELD OF THE INVENTION

The present invention relates generally to devices and methods involving the use of rate-indexed cardiac rhythm templates for discriminating arrhythmias.

BACKGROUND OF THE INVENTION

Proper cardiac function relies on the synchronized contractions of the heart at regular intervals. When the heart is functioning normally, synchronized cardiac contractions are initiated at the sinoatrial node and the heart is said to be operating in normal sinus rhythm. However, if contractions of the heart become irregular or uncoordinated, or if the contraction rate is too fast or too slow, the heart rhythm is described as arrhythmic. Cardiac arrhythmia may be caused, for example, by disease processes or from aberrant electrical conduction patterns occurring in the heart tissue. Cardiac arrhythmia impairs cardiac pumping efficiency and some types of cardiac arrhythmia can be life threatening.

A cardiac arrhythmia that originates in a region of the heart above the ventricles is denoted a supraventricular tachyarrhythmia (SVT). Atrial fibrillation and atrial flutter are examples of SVT. Both conditions are characterized by rapid, uncoordinated contractions of the atria.

Another example of SVT is sinus tachycardia, which is an increased heart rate due to exercise or a quick emotional response. In contrast to atrial fibrillation and atrial flutter, sinus tachycardia is characterized by rapid, coordinated contractions of the atria, compensating for the increased strain placed upon the body during exercise or quick emotional responses. Whereas atrial fibrillation and atrial flutter are "abnormal" (yet not lethal), sinus tachycardia is "normal" (and also not lethal).

Cardiac arrhythmias originating in a ventricular region of the heart are denoted ventricular tachyarrhythmia. Ventricular tachyarrhythmia (VT) is characterized by rapid ventricular contractions and can degenerate into ventricular fibrillation (VF). Ventricular fibrillation produces extremely rapid, non-coordinated contractions of the ventricles. Ventricular fibrillation is fatal unless the heart is returned to sinus rhythm within a few minutes.

Implantable cardiac rhythm management (CRM) devices, including pacemakers and implantable cardioverter/defibrillators, and have been used to deliver effective treatment to patients with serious cardiac arrhythmias. Cardiac rhythm management devices may treat cardiac arrhythmias with a variety of tiered therapies. These tiered therapies range from delivering low energy pacing pulses timed to assist the heart in maintaining pumping efficiency to providing high-energy shocks to treat and/or terminate fibrillation. To effectively deliver these treatments, the CRM device must first identify the type of arrhythmia that is occurring, after which appropriate therapy may be delivered to the heart.

SUMMARY OF THE INVENTION

The present invention is directed to methods and systems used for discrimination between supraventricular tachyarrhythmia (SVT) and ventricular tachyarrhythmia (VT). One embodiment of the invention is directed to a method for classifying SVT and VT rhythms. The method involves determining if a patient's supraventricular rhythm exhibits rate dependent morphology. If the patient's supraventricular rhythm is determined to exhibit rate dependent morphology, an implantable device classifies a detected tachyarrhythmia episode based on one or more templates selected from a plurality of rate-indexed templates. Determining if the supraventricular rhythm exhibits rate dependent morphology may include determining one or more rates at which a change in morphology occurs.

According to one aspect of the invention, the determination of whether or not the patient's supraventricular rhythm exhibits rate dependent morphology may be accomplished by creating supraventricular tachyarrhythmia. Creating a supraventricular tachyarrhythmia can include simulating a supraventricular tachyarrhythmia by artificially raising the patient's atrial rate or eliciting a supraventricular tachyarrhythmia by naturally raising the patient's atrial rate. Formation or updating of the plurality of rate-indexed templates may be accomplished using cardiac waveforms sensed during the created supraventricular tachyarrhythmia.

For example, the supraventricular tachyarrhythmia may be created through atrial pacing at multiple pacing rates. Cardiac waveforms are sensed during the created supraventricular tachyarrhythmia. The determination of rate dependency is made based on morphologies of the cardiac waveforms. The atrial pacing may be delivered in accordance with an automated atrial pacing pattern, such as pacing at progressively higher rates.

In another example, the supraventricular tachyarrhythmia may be created by altering patient activity under controlled conditions. According to yet another example, the supraventricular tachyarrhythmia may be created by administration of drugs to the patient.

According to another aspect of the invention the determination of whether or not the patient's supraventricular rhythm exhibits rate dependent morphology may be accomplished based on detection of spontaneous episodes of supraventricular tachyarrhythmia. The plurality of rate-indexed templates may be formed or updated based on morphologies of cardiac waveforms sensed during the spontaneous supraventricular tachyarrhythmia. The spontaneous supraventricular tachyarrhythmia episodes may be confirmed using at least one of episode morphology, onset, AV delay stability, and correspondence between atrial and ventricular rates. Alternatively, or additionally, the spontaneous supraventricular tachyarrhythmia episodes may be confirmed using a subcutaneously generated electrocardiogram signal.

In one approach, classifying the tachyarrhythmia episode may involve determining a rate of the tachyarrhythmia episode and selecting the one or more templates associated with a rate near the tachyarrhythmia episode rate.

In another approach, a template estimate is formed based on interpolation between at least two selected templates. The tachyarrhythmia episode is classified using the template estimate.

In yet another approach, an initial template is selected from the plurality of rate-indexed templates based on rate. The approach involves searching for the one or more templates used to classify the tachyarrhythmia episode based on the initial template and on morphological similarities between the one or more templates and waveforms of the tachyarrhythmia episode.

Another embodiment of the invention is directed to a medical system for discriminating between SVT and VT. The system includes sensing circuitry configured to sense cardiac waveforms. A template generator is configured to form a plurality of rate-indexed templates characterizing cardiac waveforms sensed during supraventricular tachyarrhythmia.

An arrhythmia classification processor classifies cardiac rhythms using one or more templates selected from the plurality of rate-indexed templates if the patient's supraventricular rhythm exhibits rate dependent morphology.

The medical system may also include a cardiac pacing circuit and a control system. The cardiac pacing circuit is configured to create the supraventricular tachyarrhythmia through atrial pacing. The control system is configured to determine if the supraventricular rhythm exhibits rate dependent morphology based on the cardiac waveforms sensed during the created supraventricular tachyarrhythmia. The control system is further configured to form the plurality of rate-indexed templates using the cardiac waveforms. The atrial pacing may be delivered in accordance with an automated atrial pacing pattern, such as a progressively incremented rate.

According to various implementations, the template generator is configured to form or modify the plurality of rate-indexed templates using cardiac waveforms sensed during spontaneous or created supraventricular tachyarrhythmia.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1A:
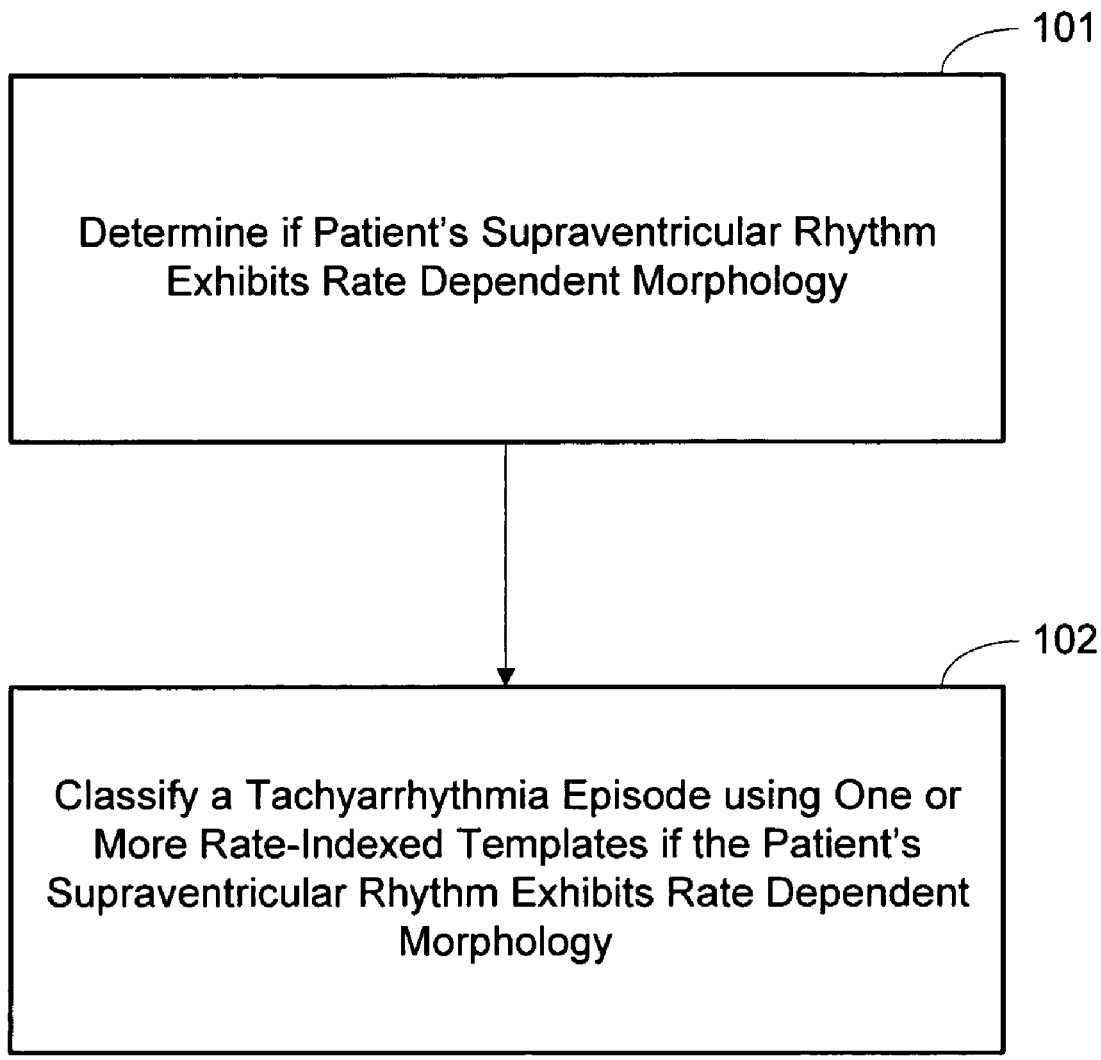
FIG. 1A is a diagram illustrating a method for SVT/VT discrimination in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings forming a part hereof, and in which are shown by way of illustration, various embodiments by which the invention may be practiced. It is to be understood that other embodiments may be utilized, and structural and functional changes may be made without departing from the scope of the present invention.

Some current medical devices discriminate between supraventricular tachyarrhythmia (SVT) episodes and ventricular tachyarrhythmia (VT) episodes based on the morphology of the cardiac electrical signals produced during the episodes. The process involves detecting a cardiac electrical signal of ventricular beats during an episode of rapid heart rate. The cardiac electrical signal of the episode is compared to a normal sinus rhythm (NSR) template using an algorithm that determines a correspondence or similarity between the morphology of the episode and template morphology. If the morphology of the episode is similar to the NSR template, the episode is diagnosed as SVT, and therapy is withheld. In contrast, if the episode morphology does not correspond with the NSR template, processes are typically performed to diagnose and verify the episode as ventricular tachycardia, after which therapy may be delivered.

Morphology-based SVT/VT discrimination processes may be confounded because some patients exhibit SVTs that produce cardiac signals having morphologies different from the NSR template. For example, patients with bundle branch block, partial AV block, or other A-V conduction problems tend to exhibit rate aberrancy, which produces rate dependent changes in cardiac signals produced by supraventricular tachyarrhythmias. Rate aberrancy presents a challenge to the specificity of SVT/VT discrimination processes if the morphology template used for discrimination is obtained under NSR conditions. The rate dependent morphology of rate aberrant SVTs may lead to false positive diagnosis of VT and inappropriate therapy delivery.

Embodiments of the invention are directed to processes that may be used to automatically discriminate SVT episodes from VT episodes based on the morphology of the SVT or VT cardiac signals while taking into account SVT rate aberrancy. The processes described herein are fully or partially implementable in an implantable cardiac rhythm management (CRM) device. FIG. 1A is a diagram illustrating a method for SVT/VT discrimination in accordance with embodiments of the invention. The method involves determining 101 if a patient's supraventricular rhythm exhibits rate dependent morphology. Tachyarrhythmia episodes are automatically classified 102 by the CRM device using one or more rate-indexed morphology templates if the patient's supraventricular rhythm exhibits rate dependent morphology.

A cardiac morphology template may be created and used to analyze or otherwise process a sensed cardiac signal for a variety of purposes, including, for example, discrimination of SVT from VT. Cardiac templates may include representative waveforms and/or information derived from waveforms, such as various attributes and/or ranges of attributes of the sensed cardiac signal, including, but not limited to: timing and/or rate information, changes in QRS width, T-wave amplitude, Q-wave amplitude, QT interval, R-R intervals, interval statistics, critical points, significant points, curvature, local extrema, inflection points, rise or fall times, slopes, areas above and/or below waveforms, areas between a waveform and a baseline, and frequency and/or wavelet coefficients, or other intervals or attributes useful for determining a correspondence between a cardiac waveform and a template.

Figure 1B:
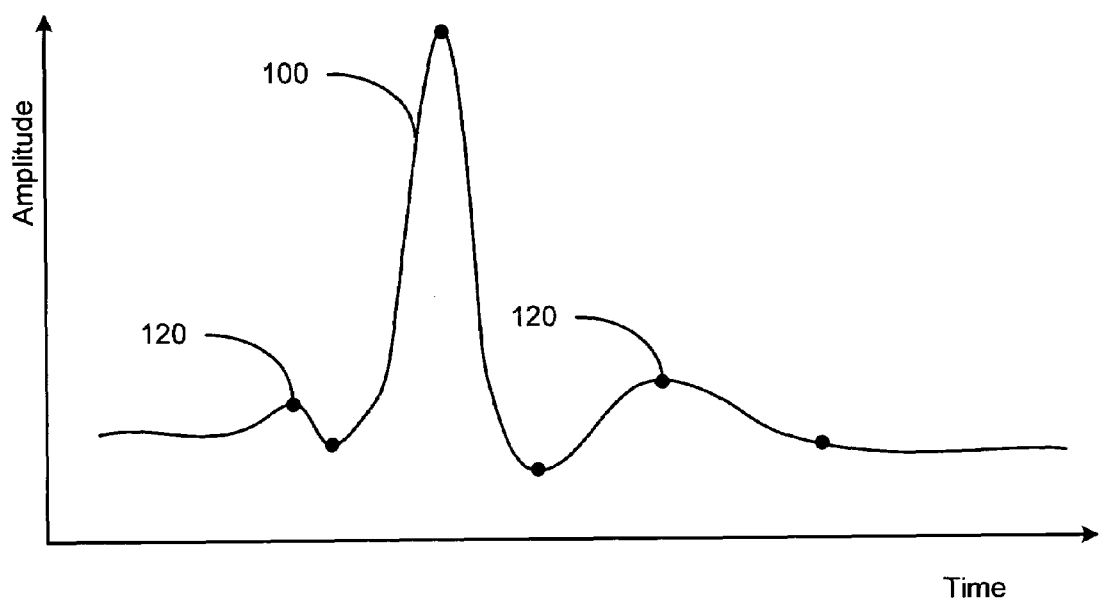
FIG. 1B illustrates the morphology of a cardiac beat waveform with identification of signal features that may be extracted for template creation and/or for comparison with templates formed using previous beats in accordance with embodiments of the invention.

In one example, the templates are formed using amplitude and timing features extracted from the cardiac beat waveforms. FIG. 1B illustrates the morphology of a cardiac beat signal waveform with identification of amplitude and timing signal features that may be extracted for template creation and/or for comparison with templates formed using previous beats in accordance with embodiments of the invention.

As illustrated in FIG. 1B, a cardiac waveform 100 representing a particular beat morphology is sensed and one or more cardiac waveform features 120 are detected. A waveform feature 120 may include a particular point of a cardiac signal waveform 100 having amplitude coordinate and a time coordinate.

Figure 2A:
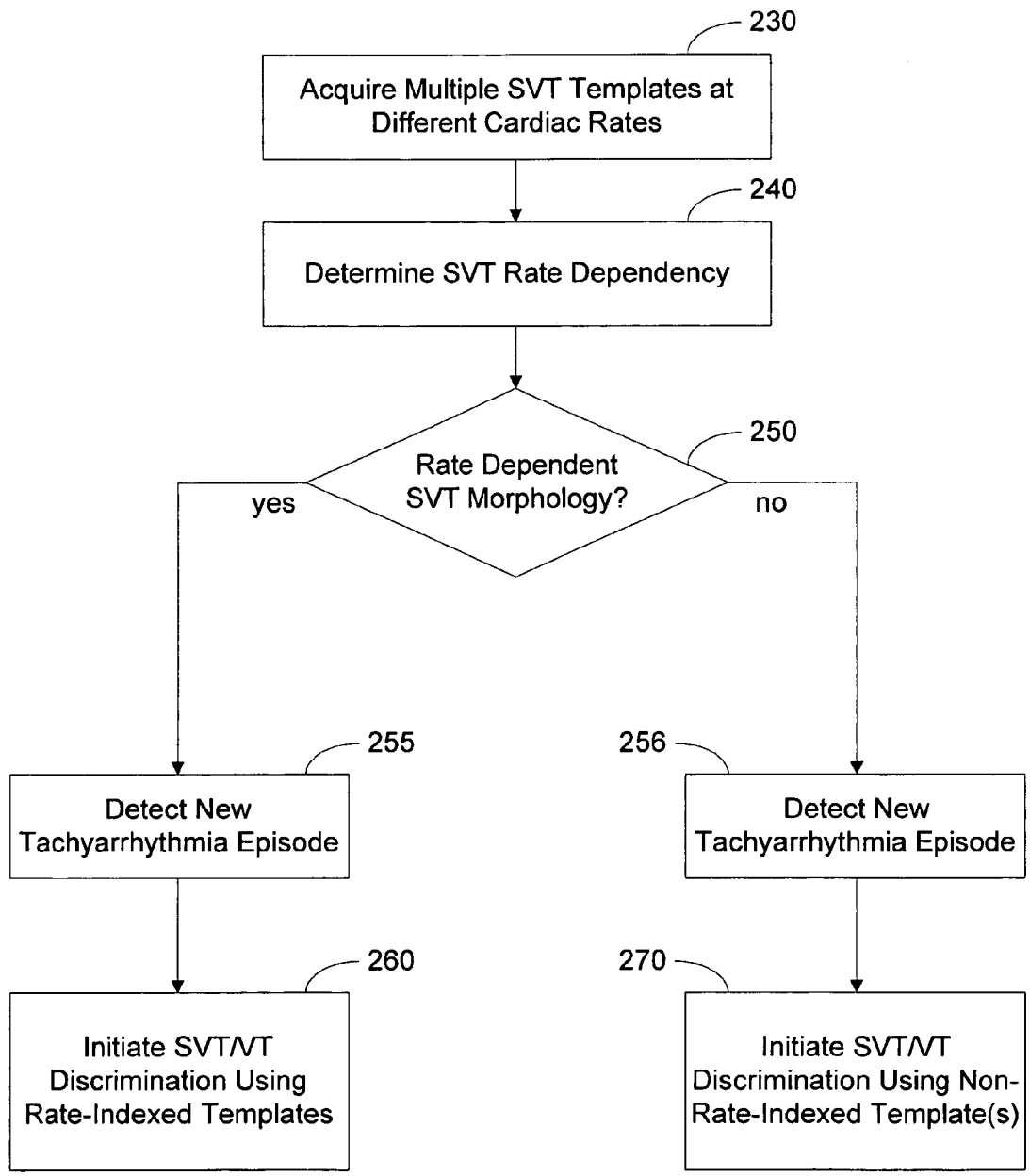
FIG. 2A is a flowchart illustrating a process for selecting a protocol for discriminating SVT from VT based on the determination of rate dependency in accordance with embodiments of the invention.

The flowchart of FIG. 2A illustrates in more detail processes for selecting a protocol for discriminating SVT from VT based on rate dependency in accordance with embodiments of the invention. Multiple SVT templates are acquired 230 at different cardiac rates. SVT may be created by atrial pacing, by exercise, or by drugs, for example. A template is acquired for various rates of SVT and the templates are indexed to the rates at which they are acquired. The templates are analyzed to determine 240 if the supraventricular rhythm of the patient exhibit rate dependent morphology. The analysis of SVT rate dependency may be performed by a human analyst, or may be performed automatically by a processor, such as a CRM device processor, or an advanced patient management processor. Alternatively, some functions of SVT rate dependency may be performed by a human analyst and a processor may perform other analysis functions.

SVT rate dependency analysis may be accomplished by comparing the morphology of cardiac beats produced at the multiple rates. In one embodiment, episodes used to acquire the templates at various rates are automatically compared for similarity. In another embodiment, the episode used to acquire one template at one rate is automatically compared for similarity to other templates acquired at other, various rates. In another embodiment, the templates acquired at various rates are automatically compared for similarity. If templates are found to be similar, the SVT morphology does not exhibit rate aberrancy in the rate range associated with the templates that are compared. In one implementation, the results of the automatic SVT rate dependency analysis may be reported to the physician along with a recommendation regarding the use of rate dependent SVT/VT discrimination. SVT/VT discrimination processes that take into account rate dependency may then be selected by the physician. In another implementation, rate dependent SVT/VT discrimination may be automatically selected or deselected by the CRM device depending on the rate dependency analysis.

If rate dependent SVT morphology is present 250, then for new tachyarrhythmia episodes that are detected 255, SVT/VT discrimination using rate-indexed templates is initiated 260. For example, the all or a subset of the templates acquired during the process indicated at block 230 may be used as the rate-indexed templates for SVT/VT discrimination. If the SVT morphology is rate independent 250, then for new tachyarrhythmia episodes that are detected 256, SVT/VT discrimination using one or more non-rate-indexed templates may be initiated 270.

Figure 2B:
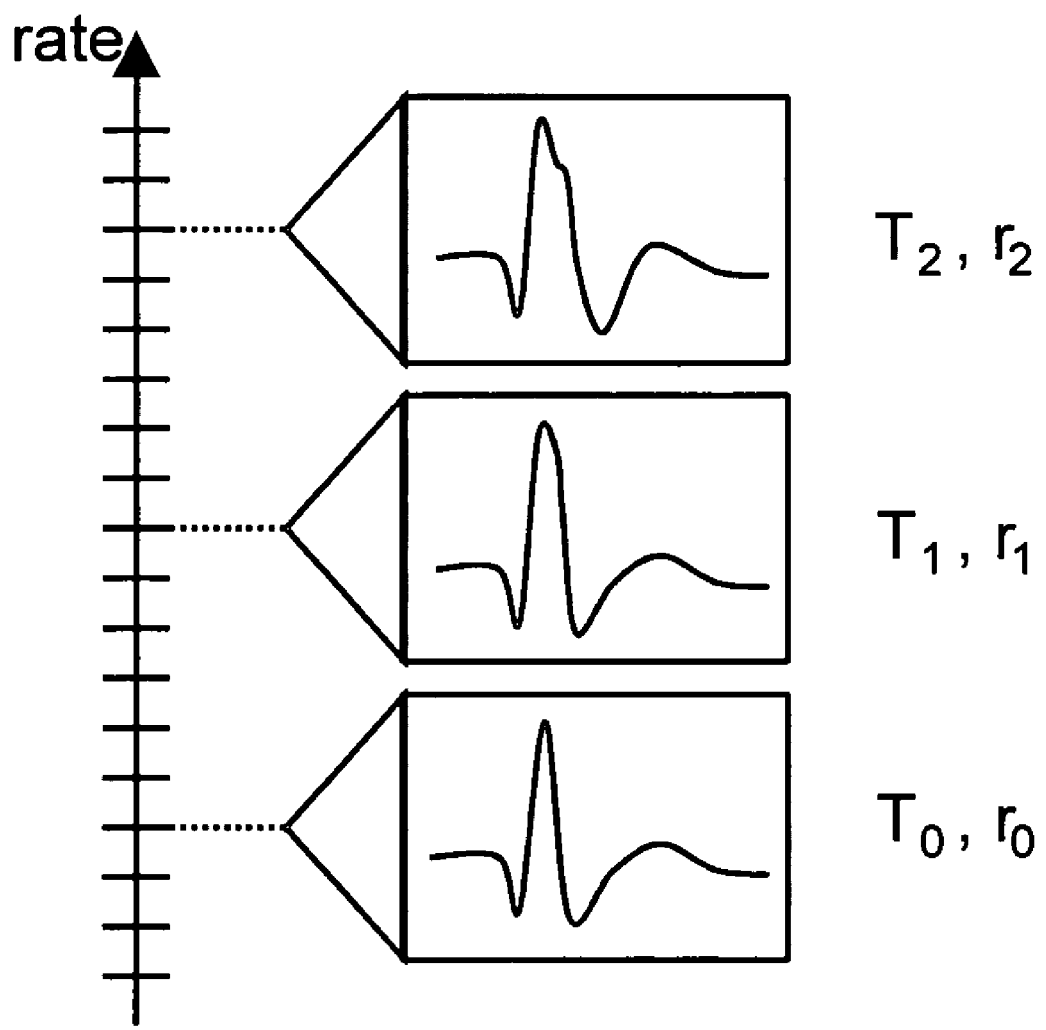
FIG. 2B illustrates rate-indexed templates in accordance with embodiments of the invention.

Acquiring a rate-indexed SVT template set may be performed at implant time of the CRM device, in the clinic or in ambulatory modes. SVT templates are automatically acquired at each of various rates. As illustrated in FIG. 2B, each template $T_0$, $T_1$, $T_2$ is stored individually, and is indexed according to its associated rate, $r_0$, $r_1$, $r_2$. Each template may be used to represent a range of rates.

Various embodiments are conceivable for automatic acquisition of the templates, either through creating an elevated sinus rate, or through triggering an automatic template capture during detected spontaneous elevated sinus rate events. The acquired templates may cover a range of rates extending from normal sinus rhythm up through a ventricular tachyarrhythmia (VT) range, and reaching as high as practically obtainable and tolerable by the patient. To conserve device memory, the increment between rates may be managed to prevent the total number of templates from becoming excessively large.

The SVT templates may be generated by extracting samples or feature points from a number of cardiac beat waveforms generated at a particular rate and averaging the corresponding samples or feature points of the cardiac beat waveforms. In some implementations, a two channel approach may be used to form the templates as described in commonly owned U.S. Pat. Nos. 6,449,503, 6,708,058, 6,889,079, and U.S. Patent Application Publication 20030181818 which are incorporated herein by reference.

In some implementations, each of the templates $T_0$, $T_1$, $T_2$ may represent multiple templates associated with the rate or rate range. More specifically, template $T_1$, may represent templates $T_{1-1}$, $T_{1-2}$, ... $T_{1-M}$. In this scenario, comparison of the cardiac waveforms associated with an SVT episode to template $T_1$ comprises comparison of the SVT cardiac waveforms to one or more of the templates $T_{1-1}$, $T_{1-2}$, ... $T_{1-M}$ represented by $T_1$.

The criterion used to form the templates, such as the number and/or type of features, may be tailored to support the various SVT morphology characteristics of the patient, e.g., bundle branch morphology. In some embodiments, one type of SVT template, generated based on acquisition of first set of characteristic features, number or timing of feature points, or other processes, may be used to discriminate SVT from VT for a first rate range, and another type of SVT template, generated based on acquisition of a second set of characteristic features, number or timing of feature points, or other processes, or may be used for a second rate range.

Figure 3:
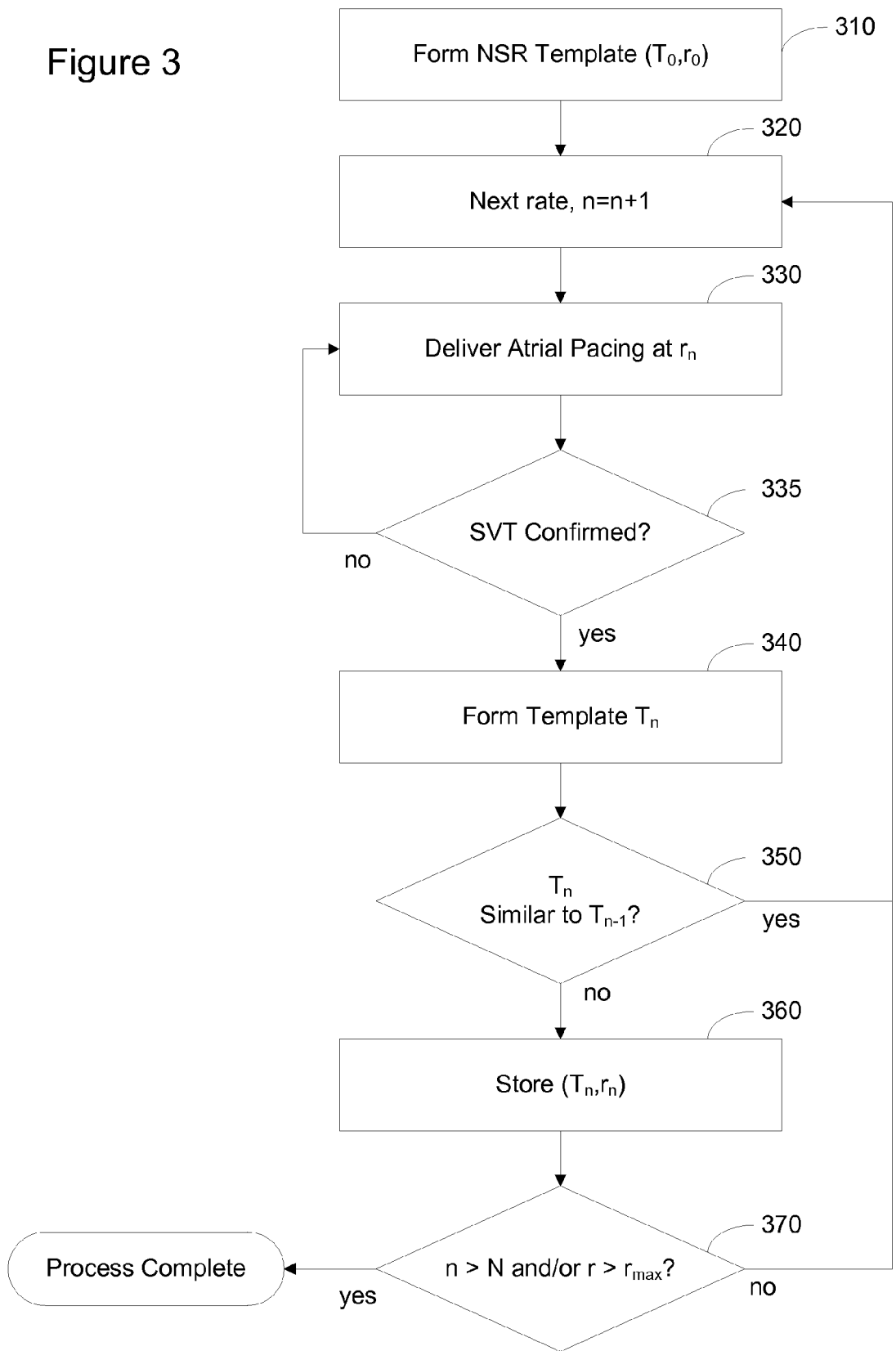
FIG. 3 is a flowchart of a method illustrating formation of rate-indexed SVT templates based on atrial pacing in accordance with embodiments of the invention.

In one embodiment, illustrated in the flowchart of FIG. 3, rate-indexed SVT templates are generated using atrial pacing. The formation of the templates may be performed at the time of device implant, follow-up, or possibly during ambulatory conditions. A template $T_0$ corresponding to the patient's NSR rate $r_0$ is formed 310. After collection of the reference NSR template, $T_0$, the atrial pacing rate is successively incremented 320. For example, the patient is paced 320, 330 in AAI mode at a set of elevated rates $r_n$, for n=1 ... N. A corresponding template $T_n$ is collected 340 at each rate for which SVT is confirmed 335. The current template, $T_n$, is compared to a template, $T_{n-1}$, acquired for the previous rate $r_{n-1}$. For example, the current and previous templates, $T_n$, $T_{n-1}$, may be compared by calculating a feature correlation coefficient (FCC) as described in U.S. Pat. Nos. 6,449,503 or 6,889,079, or commonly owned U.S. Patent Application Publication 2004/0093035 which are incorporated herein by reference. In other embodiments, the templates may be compared based on a similarity measure that is directly or indirectly proportional to the sum of the absolute value of the differences between corresponding features of the current and the previously formed template.

If the current template, $T_n$, is sufficiently similar 350 to the previous template, $T_{n-1}$ such as if the FCC is greater than about 0.94, template $T_n$ is not stored, the pacing rate is incremented 320, and a template for the next rate is acquired.

If the current template $T_n$ is not sufficiently similar 350 to the previous template $T_{n-1}$, the template $T_n$ is stored 360 and is indexed to the associated rate $r_n$. The process 320-370 continues until 370 a predetermined number of templates is acquired or until a desired rate is reached, which may be an arbitrary or physiologic maximum rate, or until it is determined that the patient does not exhibit rate dependency.

The process described in connection with FIG. 3 provides for good control of the rate used for template generation. Selectable rate resolution through pacing facilitates focusing on one or more rate bands where the SVT morphology exhibits a conduction break. The process is particularly useful as a self tuning procedure performed at implant time and may allow high patient tolerability and low patient discomfort. The morphology of AAI paced beats provides a reasonably good approximation to SVT, as it originates in the upper chamber and follows the normal condition path to the ventricle.

Processes for acquiring rate-indexed SVT templates as described above may be performed by manual, automatic, or partially automatic processes. In one implementation, the pacing rate is automatically incremented or ramped up linearly by a pacing script initiated at implant, although other methods of changing the pacing rate for template acquisition may be used. For example, the pacing rate may be iterated using a bisection or successive approximation approach. Stable and unstable SVT, including atrial flutter, sinus tachyarrhythmia, and atrial fibrillation, can be readily simulated using the AAI pulse train to develop a variety of atrial rhythms allowing determination of stability dependence in the SVT morphologies.

In one embodiment, the rate-indexed templates may be acquired by creating SVT naturally through exercise. In this implementation, the patient's rate is elevated naturally by physiologic demand under controlled conditions, using, for example, a treadmill exercise protocol. At each of a set of target rates, $r_n$, template $T_n$ is acquired over a temporally local set of beats having rates sufficiently close to $r_n$. Templates may be acquired online during this procedure, as the beats occur, or offline after the exercise protocol is completed. For example, acquisition of templates may involve processing an entire electrogram (EGM) record using the CRM device programmer or remote server, and then downloading the rate-indexed SVT template set to the CRM device.

Figure 4:
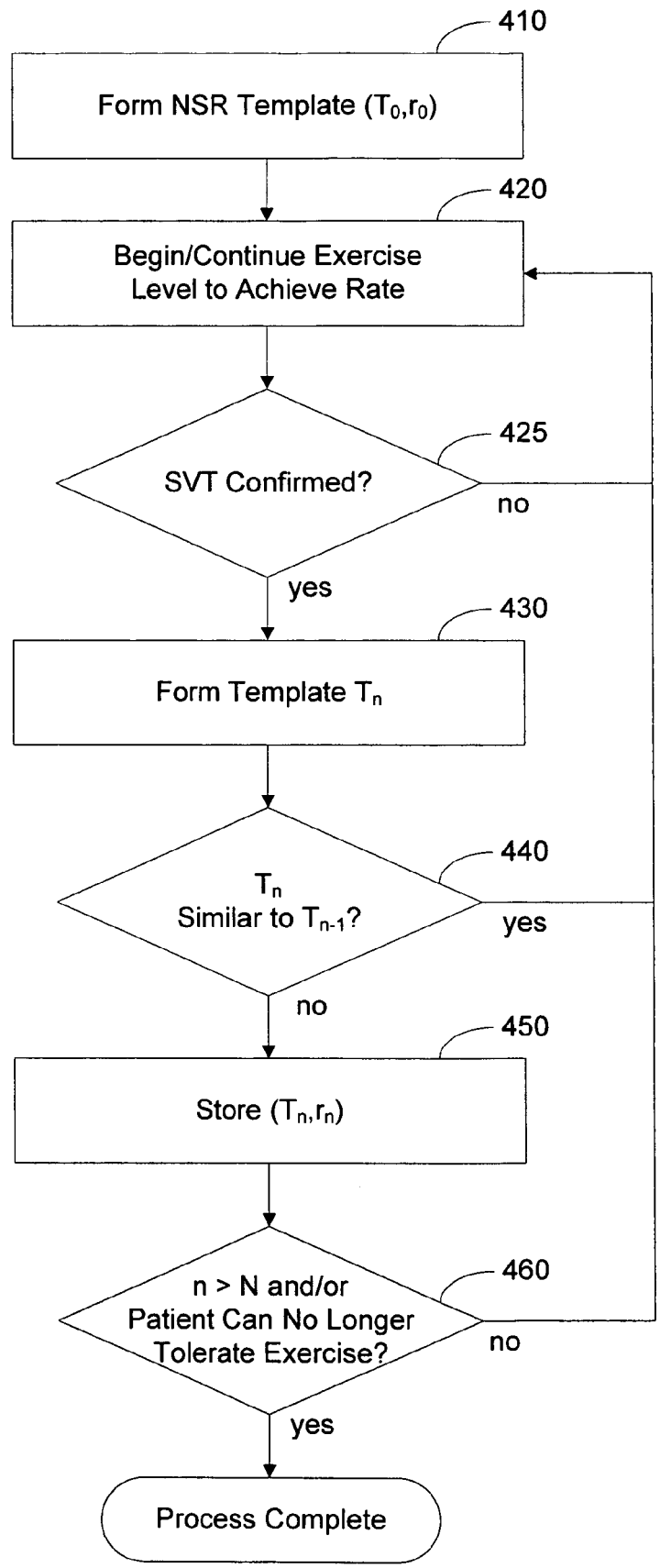
FIG. 4 is a flowchart of a method illustrating formation of rate-indexed SVT templates through natural creation of SVT in accordance with embodiments of the invention.

FIG. 4 provides a method for acquisition of SVT templates through natural creation of SVT through exercise in accordance with an embodiment of the invention. An NSR template, $T_0$, is formed 410 while the patient's heart rate is at the rest rate (rate=$r_0$). After collection of the reference NSR template, $T_0$, the patient begins 420 the exercise protocol to increase the patient's heart rate. If SVT is confirmed 425, a SVT template, $T_n$, is acquired 430 at the elevated rate. If the template, $T_n$, is similar 440 to the template acquired at a previous rate, which in the first iteration is $r_0$, then the patient's exercise level is increased 420 to create a higher rate SVT. If the template, $T_n$, acquired during the exercise is not similar 440 to a previously acquired template of the next lower rate, $T_{n-1}$, then the template $T_n$ is stored and indexed to the rate $r_n$. The template acquisition process 420-450 may continue until a predetermined number of templates is acquired, until the patient can no longer tolerate exercise, or until it is determined that the patient does not exhibit rate dependency.

Because the beats originate from the patient's own sinus, SVTs generated through exercise may more closely represent stable SVT than SVT beats generated through atrial pacing. As a result, the SVT beat morphology templates acquired through natural creation of SVT may more closely represent the patient's natural, stable supraventricular rhythms. However, rate control for SVTs created via the natural process is more difficult than if atrial pacing is used. For example, specific rates, such as conduction break rates, may not be achievable with as much precision or repeatability. Further, unstable SVT rhythms may not be obtainable through naturally created SVT.

In another embodiment, SVTs may be created and templates collected in a similar fashion to the SVTs created via exercise by electrical stimulation or drugs administered in a clinic. Acquisition of unstable SVT rhythms may be more feasible with this method than using creation of SVT through exercise. However, the resulting morphology may be influenced by the creating mechanism.

Figure 5:
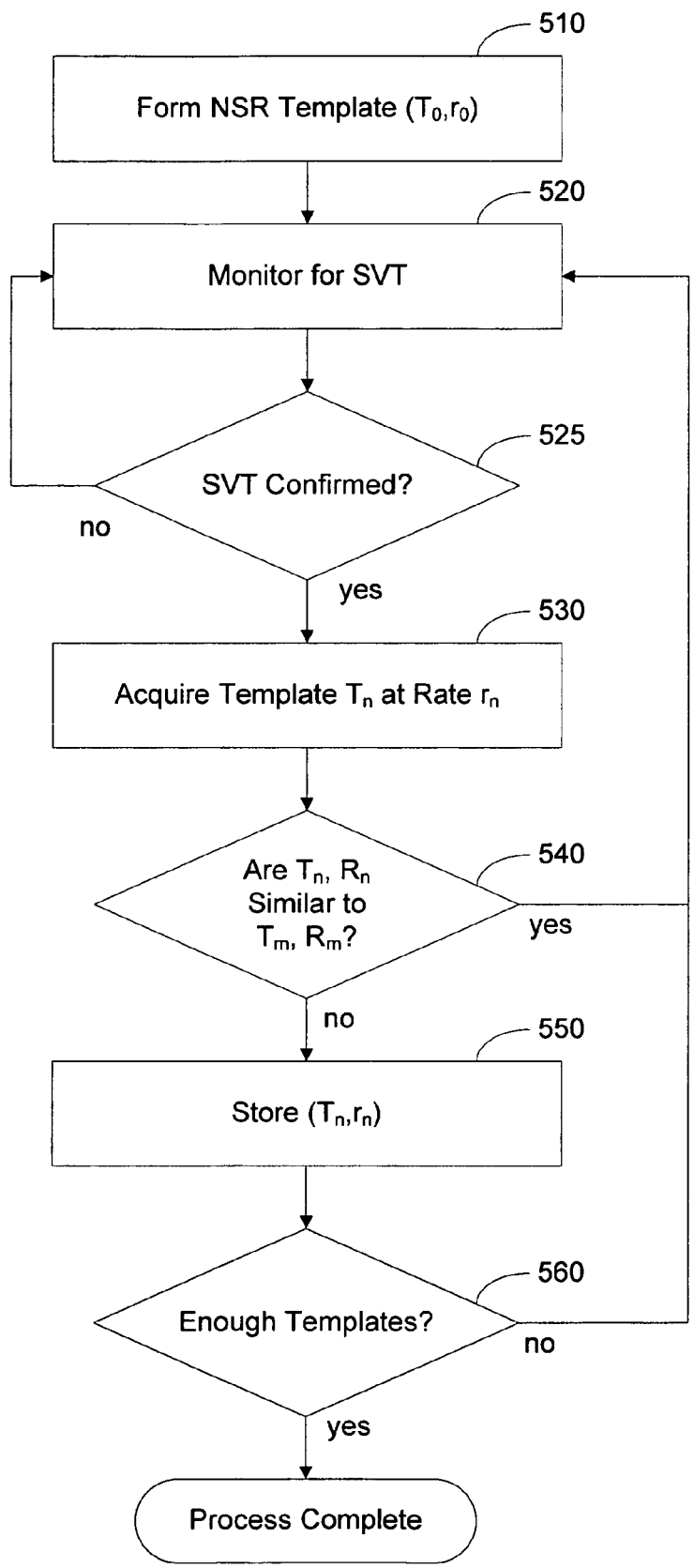
FIG. 5 is a flowchart of a method providing acquisition of rate-indexed SVT templates using spontaneously occurring SVTs in accordance with an embodiment of the invention.

In a further embodiment, illustrated in FIG. 5, the patient's cardiac rhythm is monitored while the patient is ambulatory and templates are acquired from spontaneously occurring SVTs. Using this approach alone, SVT templates for various rates are only acquired when the rates spontaneously occur. Thus, the first time an SVT episode at a particular rate occurs no template is available for SVT/VT discrimination if rate dependent discrimination is enabled.

Acquisition of a rate-indexed SVT template set based on spontaneous SVTs set may be triggered, either manually or automatically. For example, acquisition of the SVT template set may be automatically triggered after a number of SVTs have been detected, or after an arbitrary time period following implant. In one implementation, rate-indexed SVT templates are automatically acquired under conditions of confirmed SVT and morphology change. For example, detected changes in morphology of SVT rhythms may trigger collection of a rate-indexed SVT templates. The process illustrated in FIG. 5 may be implemented as an automatic process for acquiring rate-indexed SVT templates. The automated approach follows the patient's lifestyle and collects representative sinus tachyarrhythmia rates and morphologies.

An NSR template, $T_0$, is acquired 510 at the resting rate, $r_0$. The patient's cardiac rhythm is monitored 520 for the occurrence of SVT. If an SVT episode is detected, the episode is confirmed 525. SVT confirmation may be based on episode morphology, onset, stability, 1:1 correspondence between atrial and ventricular rates, consistency with sensor indicated rate, and/or stability of AV delay, for example. Confirmation of SVT may be accomplished by automated monitoring of a surface or wireless electrocardiogram (ECG) to verify that p waves occur before a majority of ventricular beats.

A template $T_n$ is acquired 530 at rate $r_n$ during the SVT episode. If the acquired template $T_n$ is not similar 540 to another template $T_m$, or if rate $r_m$ associated with $T_m$ is outside a predetermined range of $r_n$, then the template $T_n$ and rate $r_n$ are stored. If acquired template $T_n$ is similar 540 to $T_m$, and rate $r_m$ is within a predetermined range of $r_n$, then the template $T_n$ and rate $r_n$ are not stored. The process 520-560 continues until a predetermined number of templates is acquired, and/or until it is determined that no appreciable SVT rate dependency exists.

A patient's SVT morphology may change over time, for example, due to a change in medication or cardiac condition.

To accommodate changes in SVT morphology, the set of SVT templates may also be periodically or occasionally updated using exercise, drugs, or automatically or manually triggered atrial pacing. The set of SVT templates may be periodically or occasionally updated using spontaneous SVTs, as part of an arrhythmia memory feature. Embodiments of the present invention may incorporate various processes for generating and updating SVT templates described in commonly owned U.S. Patent Application Publication 2004/0093035 and U.S. patent application Ser. No. 10/996,340, filed Nov. 23, 2004, which are incorporated herein by reference. The set of SVT templates can be updated using newly generated templates. Newly generated templates within a corresponding rate range could replace older templates in the SVT template set.

Figure 6:
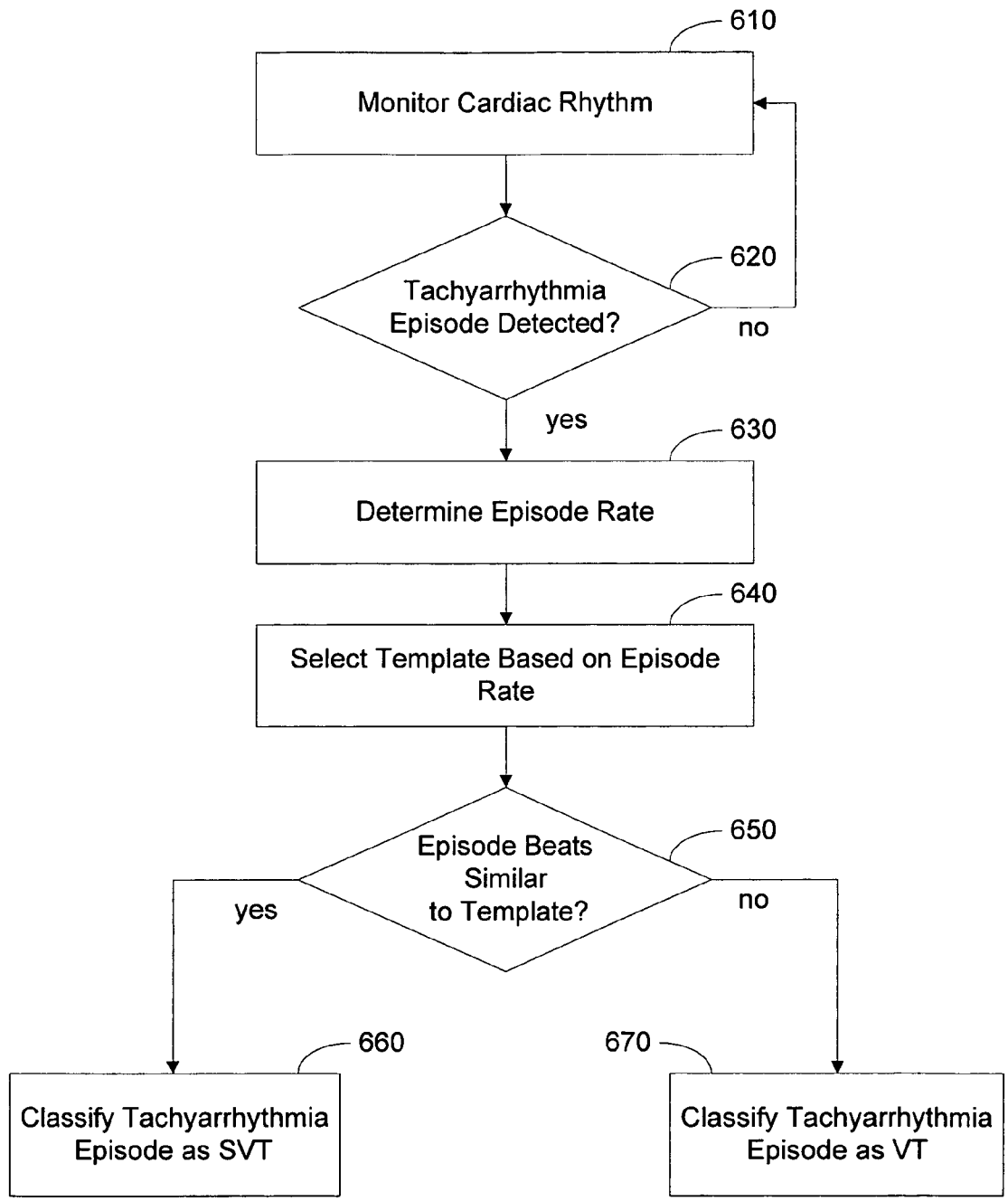
FIG. 6 is a flowchart illustrating classification of cardiac rhythms following initiation of SVT/VT discrimination based on rate-indexed SVT templates in accordance with embodiments of the invention.

After acquisition of the rate-indexed templates, for example, by any of the processes described in connection with FIGS. 3-5, by a combination of the processes described in connection with FIGS. 3-5, or by other processes, the rate-indexed templates may be used for SVT/VT discrimination. The flowchart of FIG. 6 illustrates classification of cardiac rhythms following initiation of SVT/VT discrimination processes using rate-indexed SVT templates in accordance with embodiments of the invention.

The patient's cardiac rhythm is monitored 610. If a tachyarrhythmia episode is detected 620, the episode rate is estimated 630. An SVT template is selected 640 based on the episode rate. The morphology of the cardiac signal detected during the tachyarrhythmia episode is compared to the selected SVT template. If the episode morphology is sufficiently similar 650 to the template, the episode is classified 660 as SVT. If the episode morphology is not sufficiently similar 650 to the template, the episode is classified 670 as VT.

In some implementations, estimation of the rate may be accomplished using the last beat interval, or from a local average of beat intervals. If the rate estimation is performed using the last beat interval, then the template selection 640 and SVT/VT discrimination 650 may be performed beat to beat. If the local average is used, then template selection 640 and SVT/VT discrimination 650 may be performed either beat to beat or over a neighborhood of beats temporally close to the beats used to determine the estimated rate.

According to one embodiment, the template is selected for SVT/VT discrimination based on rate using a table look up. In one example, the template associated with a rate closest to the estimated episode rate is selected. In another example, the template associated with the next lowest rate to the estimated episode rate is selected. The latter example is useful for patients whose conduction pattern tends to break at a certain critical rate.

According to another embodiment, a template estimate is generated from two or more rate-indexed templates, producing an estimated template having increased rate resolution. For example, the estimated template may be produced by linear or non-linear interpolation of the corresponding samples or feature points of two or more templates with the interpolation parameter as the episode rate. The effective rate resolution enhancement acquired by this method may be especially advantageous over rate regions where the underlying SVT morphology is particularly sensitive to changes in rate.

According to a further embodiment, a template estimate may be performed by rate perturbation matching. The template associated with a rate closest to the episode rate may be initially selected. The initially selected template could be used as a starting point for a search to find a template that matches the episode morphology. The template search may be achieved using a steepest descent method, for example. If a matching template is found, then the episode is classified as an SVT.

Although a number of the embodiments describe template generation and template matching based on amplitude and timing correlation of cardiac beat waveforms and template features, various methods of generating and using templates for rhythm discrimination are equally applicable. Other useful methods and systems for classifying cardiac complexes based on morphological features are described in commonly owned U.S. Pat. Nos. 6,223,078, 6,275,732, 6,266,554, 6,449,503, 6,684,100, and 6,434,417 which are incorporated herein by reference.

Embodiments of the present system illustrated herein are generally described in connection with a patient internal CRM device, which may operate in numerous cardioversion/defibrillation and pacing modes known in the art. Various types of single and multiple chamber CRM devices may be used to implement a number of pacing therapies as are known in the art, in addition to cardioversion/defibrillation therapies. A CRM device may implement various anti-tachyarrhythmia therapies, such as tiered anti-tachyarrhythmia pacing and/or defibrillation therapies, which are initiated through morphological SVT/VT discrimination analyses.

It is understood that configurations, features, and combination of features described in the present disclosure can be implemented in a wide range of implantable or external medical devices, and that such embodiments and features are not limited to the particular devices described herein. The systems and methods described herein may be implemented in a variety of implantable or external diagnostic and/or therapeutic cardiac devices such as defibrillators, cardioverters, pacemakers, cardiac monitors, and resynchronizers, for example. In some embodiments, some particular features may be performed in a patient-internal device, such as a CRM device, and other particular features may be performed in a patient external device. For example, in some configurations, functions related to template processing may be performed in a patient-external device such as a device programmer or advanced patient management server. In another example, atrial pacing may be performed using an external pacing stimulator. In yet another example, atrial pacing may be performed using an implanted pacing stimulator. If still another example, a patient-external recorder may be used to record and archive the created SVT waveforms and their corresponding templates. Various combinations of patient-external and patient-internal functionality can be envisioned and is considered to be within the scope of the invention.

In one embodiment, the CRM device is configured as a single chamber device that operates to process cardiac waveforms according to a template methodology in accordance with the principles of the present invention. In another embodiment, the CRM device is configured as a dual chamber device. In yet another embodiment, the CRM device is configured to sense and/or provide electrical stimulation to multiple heart chambers, for example, both ventricles of the heart, as in a resynchronizer used to treat congestive heart failure (CHF).

Figure 7:
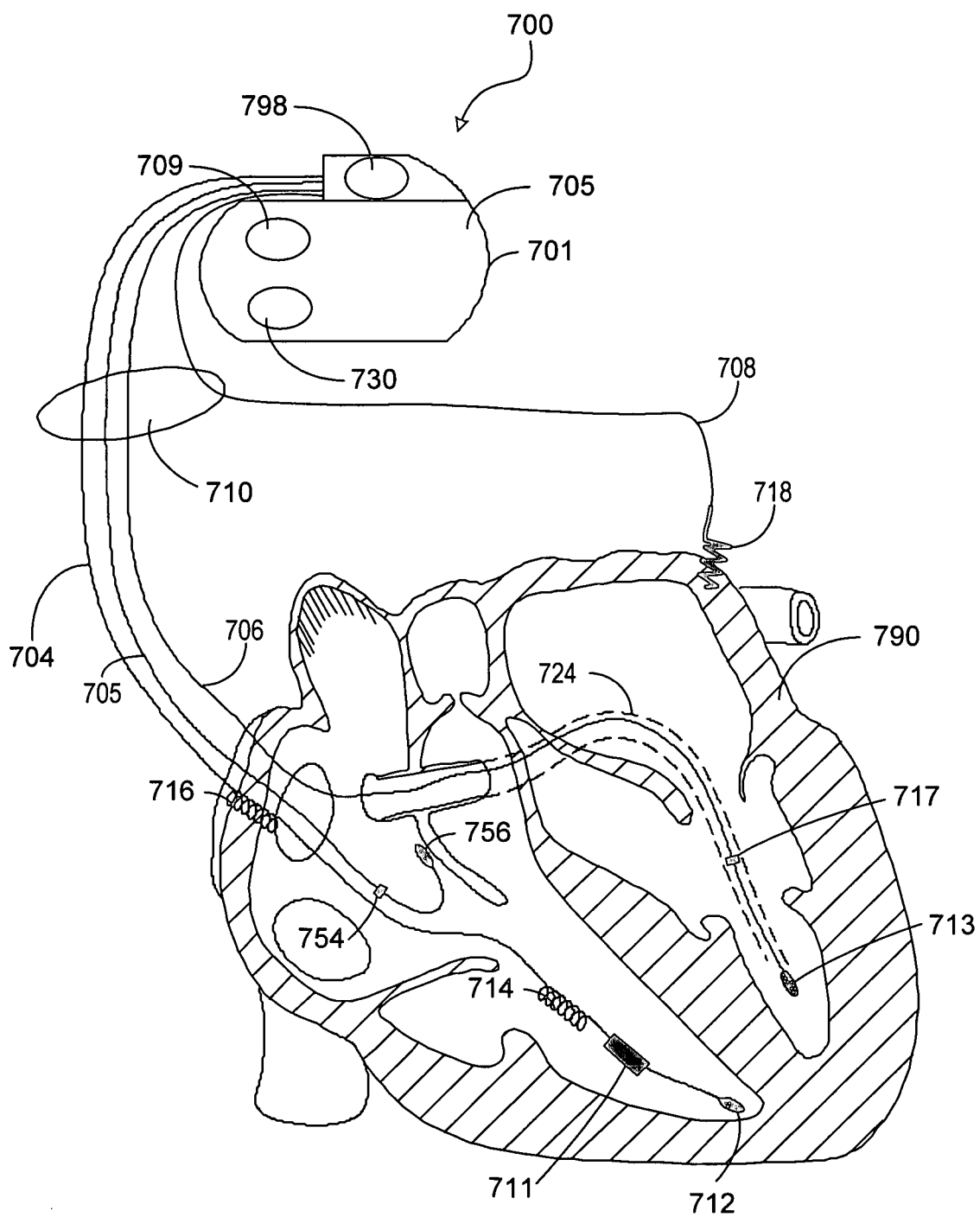
FIG. 7 is a partial view of one embodiment of an implantable medical device that may be used to implement SVT/VT discrimination taking into account SVT rate dependency in accordance with embodiments of the invention.

Referring now to FIG. 7 of the drawings, there is shown one embodiment of a system that may be used to implement tachyarrhythmia therapy selection methods of the present invention. The cardiac rhythm management system in FIG. 7 includes a CRM device 700 electrically and physically coupled to a lead system 710. The housing and/or header of the CRM device 700 may incorporate one or more electrodes 798, 709 used to provide electrical stimulation energy to the heart and/or to sense cardiac electrical activity. The CRM device 700 may utilize all or a portion of the CRM device housing as a can electrode 709. The CRM device 700 may include an indifferent electrode 798 positioned, for example, on the header or the housing of the CRM device 700. If the CRM device 700 includes both a can electrode 709 and an indifferent electrode 798, the electrodes 798, 709 typically are electrically isolated from each other.

Electrodes, such as the can electrode 709 and indifferent electrode 798 located on the housing or header of the CRM device 700 may be configured as subcutaneous electrodes used to acquire ECG data and waveform tracings without the need for surface ECG electrodes.

The CRM device 700 may include a sensor 730, such as an accelerometer, minute ventilation sensor, or other sensor, that provides for sensing the patient's activity or metabolic need. The sensor 730 may include components disposed, for example, within or on the CRM device housing and/or on a lead coupled to the CRM device 700. The sensor 730 generates a signal corresponding to the patient's activity level or metabolic need. The generated signal provides an indication of the pacing rate appropriate to meet the hemodynamic requirements of the patient.

The lead system 710 is used to detect electric cardiac signals produced by the heart 790 and to provide electrical energy to the heart 790 under certain predetermined conditions to treat cardiac arrhythmias. The lead system 710 may include one or more electrodes used for pacing, sensing, and/or defibrillation. In the embodiment shown in FIG. 7, the lead system 710 includes an intracardiac right ventricular (RV) lead system 704, an intracardiac right atrial (RA) lead system 705, a transvenous left ventricular (LV) lead system 706, and an extracardiac left atrial (LA) lead system 708. The lead system 710 of FIG. 7 illustrates one embodiment that may be used in connection with the SVT/VT discrimination methodologies described herein. Other leads and/or electrodes may additionally or alternatively be used.

The lead system 710 may include leads 704, 705, 706 implanted in a human body with portions of the leads 704, 705, 706 inserted into a heart 790. The leads 704, 705, 706 include various electrodes positionable in relation to the heart 790 for sensing electrical activity of the heart and for delivering electrical stimulation energy to the heart, for example, pacing pulses and/or defibrillation shocks to treat various arrhythmias of the heart.

As illustrated in FIG. 7, the lead system 710 may include one or more extracardiac leads 708 having electrodes, e.g., an epicardial electrode 718, positioned at locations outside the heart for sensing and/or pacing one or more heart chambers.

The right ventricular lead system 704 illustrated in FIG. 7 includes a superior vena cava coil (SVC-coil 716, an RY-coil 714, an RY-ring electrode 711, and an RV-tip electrode 712. The right ventricular lead system 704 extends through the right atrium and into the right ventricle. In particular, the RV-tip electrode 712, RV-ring electrode 711, and RY-coil electrode 714 are positioned at appropriate locations within the right ventricle for sensing and delivering electrical stimulation pulses to the heart. The SYC-coil 716 is positioned at an appropriate location within the right atrium chamber of the heart 790 or a major vein leading to the right atrial chamber of the heart 790.

In one configuration, the RV-tip electrode 712 referenced to the can electrode 709 may be used to implement unipolar pacing and/or sensing in the right ventricle. Bipolar pacing and/or sensing in the right ventricle may be implemented using the RV-tip 712 and RV-ring 711 electrodes. For example, a tip-to-ring vector may be used to discriminate between VT and SVT, such as by using the rate-indexed template described herein. In other implementations, the tip-to-ring vector and the RY-coil to SYC-coil/can vector may be used to discriminate between VT and SVT. (For example, where the SYC-coil is electrically tied to the can.)

In yet another configuration, the RV-ring 711 electrode may optionally be omitted, and bipolar pacing and/or sensing may be accomplished using the RV-tip electrode 712 and the RY-coil 714, for example. The right ventricular lead system 704 may be configured as an integrated bipolar pace/shock lead. The RY-coil 714 and the SYC-coil 716 are defibrillation electrodes.

The left ventricular lead 706 includes an LV distal electrode 713 and an LV proximal electrode 717 located at appropriate locations in or about the left ventricle for pacing and/or sensing the left ventricle. The left ventricular lead 706 may be guided into the right atrium of the heart via the superior vena cava. From the right atrium, the left ventricular lead 706 may be deployed into the coronary sinus ostium, the opening of the coronary sinus. The lead 706 may be guided through the coronary sinus to a coronary vein 724 of the left ventricle. This vein is used as an access pathway for leads to reach the surfaces of the left ventricle that are not directly accessible from the right side of the heart. Lead placement for the left ventricular lead 706 may be achieved via subclavian vein access and a preformed guiding catheter for insertion of the LV electrodes 713, 717 adjacent to the left ventricle.

Unipolar pacing and/or sensing in the left ventricle may be implemented, for example, using the LV distal electrode 713 referenced to the can electrode 109. The LV distal electrode 713 and the LV proximal electrode 717 may be used together as bipolar sense and/or pace electrodes for the left ventricle. The left ventricular lead 706 and the right ventricular lead 704, in conjunction with the CRM device 700, may be used to provide cardiac resynchronization therapy such that the ventricles of the heart are paced substantially simultaneously, or in phased sequence, to provide enhanced cardiac pumping efficiency for patients suffering from heart failure.

The right atrial lead 705 includes a RA-tip electrode 756 and an RA-ring electrode 754 positioned at appropriate locations in the right atrium for sensing and pacing the right atrium. In one configuration, the RA-tip 756 referenced to the can electrode 709, for example, may be used to provide unipolar pacing and/or sensing in the right atrium. In another configuration, the RA-tip electrode 756 and the RA-ring electrode 754 may be used to effect bipolar pacing and/or sensing.

FIG. 7 illustrates one embodiment of a left atrial lead system 708. In this example, the left atrial lead 708 is implemented as an extracardiac lead with an LA distal electrode 718 positioned at an appropriate location outside the heart 190 for sensing and pacing the left atrium. Unipolar pacing and/or sensing of the left atrium may be accomplished, for example, using the LA distal electrode 718 to the can 709 pacing vector. The left atrial lead 708 may be provided with additional electrodes used to implement bipolar pacing and/or sensing of the left atrium.

Figure 8:
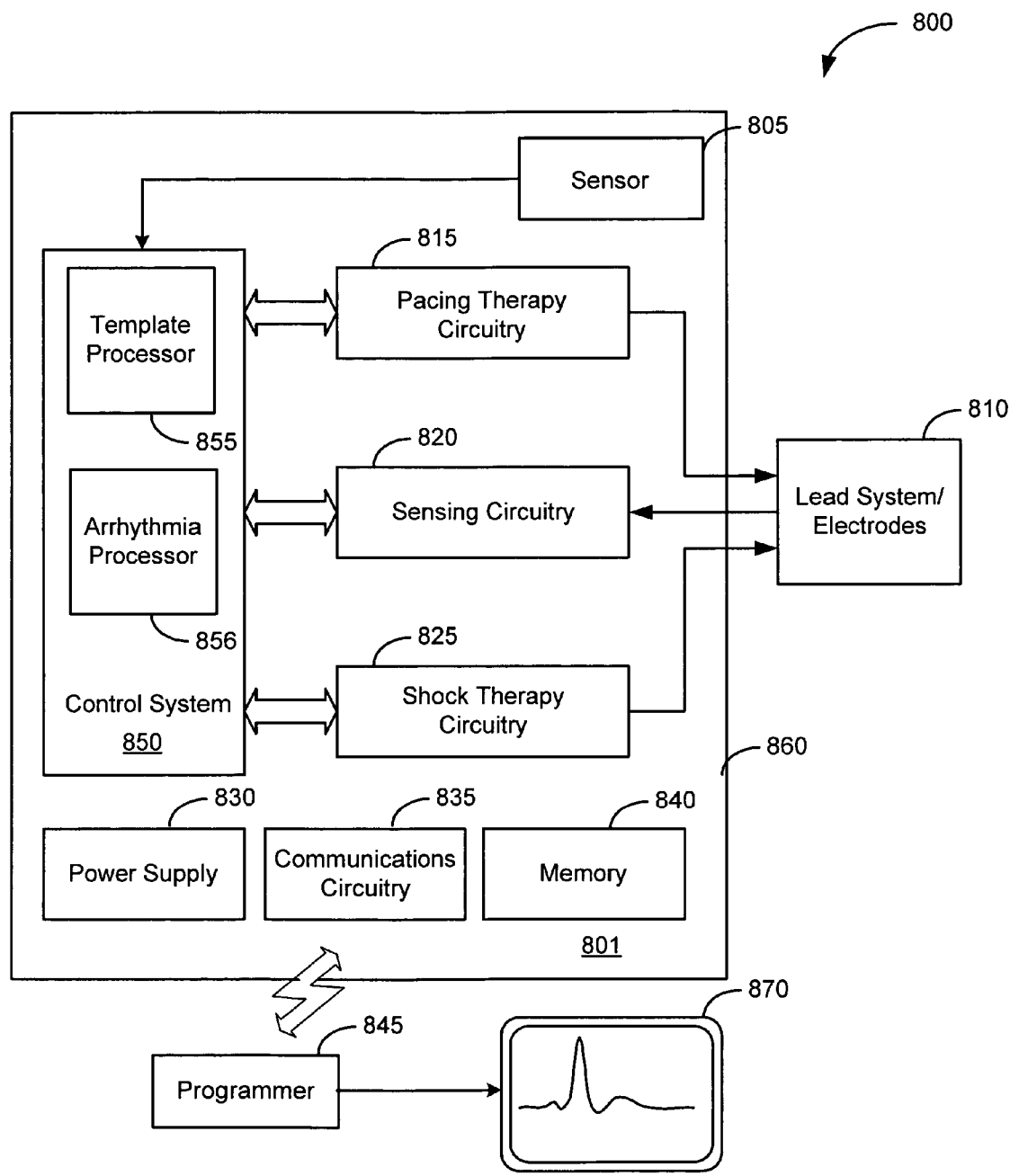
FIG. 8 is a block diagram illustrating functional components of an implantable medical device with which discrimination between SVT and VT may be implemented in accordance with embodiments of the present invention.

Referring now to FIG. 8, there is shown a block diagram of an embodiment of a system 800 employing a CRM device 860 suitable for implementing template generation, SVT rate dependency analysis, and/or SVT/VT discrimination processes of the present invention. FIG. 8 shows the system 800 divided into functional blocks. There exist many possible configurations in which these functional blocks can be arranged. The example depicted in FIG. 8 is one possible functional arrangement. The system 800 includes circuitry for receiving cardiac signals from a heart and delivering electrical energy in the form of pace pulses or cardioversion/defibrillation pulses to the heart.

A cardiac lead system 810 may be implanted so that cardiac electrodes contact heart tissue as described above in connection with FIG. 7. The cardiac electrodes of the lead system 810 sense cardiac signals associated with electrical activity of the heart. The sensed cardiac signals may be transmitted to a CRM device 860 through the lead system 810. The cardiac electrodes and lead system 810 may be used to deliver electrical stimulation generated by the CRM device 860 to the heart to mitigate various cardiac arrhythmias. The CRM device 860, in combination with the cardiac electrodes and lead system 810, may detect cardiac signals and deliver therapeutic electrical stimulation to any of the left and right ventricles and left and right atria, for example. A can electrode and/or indifferent electrode coupled to a housing of the CRM device 860 may additionally be used to sense cardiac signals, including subcutaneous ECG signals, and may also be used to deliver electrical stimulation to the heart.

In one embodiment, CRM circuitry 801 is encased in a hermetically sealed housing suitable for implanting in a human body. Power is supplied by an electrochemical battery 830 that is disposed within the housing of the CRM device 860. In one embodiment, the CRM circuitry 801 is a programmable microprocessor-based system, including a control system 850, sensing circuit 820, pacing therapy circuit 815, shock therapy circuit 825, and memory 840. The memory 840 may be used, for example, to store SVT template information, parameters for various pacing, defibrillation, and sensing modes, and data associated with sensed cardiac signals or other information. The parameters and data stored in the memory 840 may be used on-board for various purposes and/or transmitted via telemetry to an external programmer unit 845 or other patient-external devices, as desired.

The control system 850 may used to control various subsystems of the CRM device 860, including the pacing therapy circuit 815, the shock therapy circuitry 825, and the sensing circuitry 820. The control system 850 may also include a template processor 855 for implementing a template initiation, template generation, and template updating according to embodiments of the invention.

Communications circuitry 835 allows the CRM device 860 to communicate with an external programmer unit 845 and/or other patient-external system(s). In one embodiment, the communications circuitry 835 and the programmer unit 845 use a wire loop antenna and a radio frequency telemetric link to receive and transmit signals and data between the programmer 845 and communications circuitry 835. In this manner, programming commands may be transferred to the CRM device 860 from the programmer 845 during and after implant. In addition, stored cardiac data may be transferred to the programmer unit 845 from the CRM device 860, for example.

Sensing circuitry 820 detects cardiac signals sensed at the cardiac electrodes 810. The sensing circuitry may include, for example, amplifiers, filters, A/D converters and other signal processing circuitry. Cardiac signals processed by the sensing circuitry may be communicated to the control system 850 and to the template processor 855.

The control system 850 is coupled to the template processor 855 and uses templates created and maintained by the template processor 855 to perform various functions, including, for example, SVT/VT discrimination. An arrhythmia processor 856 of the control system 850 may compare cardiac signals detected through the sensing circuitry 820 to the templates created and maintained by the template processor 855 to detect various cardiac arrhythmias, and to discriminate between SVT and VT using the rate-indexed SVT templates maintained by the template generator 855.

The pacing therapy circuit 815 is controlled by a pacemaker in the control system 850 and may be used to deliver pacing stimulation pulses to the heart through one or more of the cardiac electrodes, according to a pre-established pacing regimen under appropriate conditions.

The shock therapy circuit 825 and pacing therapy circuit 815 are coupled to the control system 850. The shock therapy circuit 825 may be used to deliver high-energy electrical stimulation to the heart to terminate or mitigate cardiac arrhythmias such as atrial or ventricular tachycardia or fibrillation detected by the control system 850.

The CRM device 860 may include a metabolic sensor 805, which may be configured as an accelerometer, minute ventilation sensor, or other sensor. The sensor 805 generates a signal corresponding to the patient's activity level or metabolic need. The signal may be used by the control system 850 to adjust a pacing rate to support the hemodynamic requirements of the patient. In one embodiment, the sensor output may be used to confirm SVT episodes. The control system 850 may optionally confirm SVT episodes based on episode onset, stability, 1:1 correspondence between atrial and ventricular rates, and/or stability of AV delay, or by other methods.

The CRM device 860 may optionally be coupled to a display device 870 capable of displaying various information related to template creation, template maintenance, and/or cardiac rhythm analysis using morphological templates, as well as other information. For example, the display device 870 may depict a graphical display of one or more detected cardiac waveforms along with the templates used to analyze or classify the detected cardiac waveforms. The display may show various data regarding the number of SVT templates used by the CRM device 860, including, for example, statistics relating to the frequency particular templates were used to analyze or classify cardiac waveforms. Other uses for the display 870 in connection with the template creation, updating and use in accordance with embodiments of the invention are also possible.

The CRM systems illustrated in FIGS. 7 and 8 provide exemplary embodiments for implementing the arrhythmia discrimination functions of the present invention. Various combinations of patient-external and implantable components may be used for implementation of arrhythmia discrimination as described herein. For example, some functionality may be implemented in an implantable device and other functionality may be implemented in a patient-external device. As such, the invention is not limited to the specific location of various components provided in the illustrative embodiments. For example, in one embodiment, one or both of the template processor and the arrhythmia processor described herein may be located in a patient-external device such as an advanced patient management system or a device programmer. In another embodiment, the cardiac electrodes used for pacing and sensing may be located in appropriate locations on the surface of the patient, or may be subcutaneously located. Circuitry used for sensing cardiac waveforms may be located in an external cardiac monitor. Circuitry used for pacing, such as creating SVTs through atrial pacing, may be located in an external pacing stimulator. Various other combinations of patient-external and implantable components used to perform the arrhythmia discrimination processes of the present invention are envisioned.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method of discriminating between supraventricular and ventricular tachyarrhythmia, comprising:
   obtaining a plurality of cardiac templates from supraventricular cardiac waveforms and associating the plurality of cardiac templates with a plurality of cardiac rates to provide a plurality of rate-indexed templates;
   detecting a tachyarrhythmia episode of a patient;
   determining an episode cardiac rate for the detected tachyarrhythmia episode;
   identifying a closest cardiac rate from the plurality of cardiac rates that is closest to the episode cardiac rate;
   initially selecting from the plurality of rate-indexed templates an initial template associated with the closest cardiac rate;
   classifying the tachyarrhythmia episode as supraventricular tachyarrhythmia or ventricular tachyarrhythmia based on one or more templates selected from the plurality of rate-indexed templates, staffing with the initial template;
   creating supraventricular tachyarrhythmia in the patient by atrial pacing at multiple pacing rates;
   sensing cardiac waveforms during the created supraventricular tachyarrhythmia; and
   determining if the patient's supraventricular rhythm exhibits rate dependent morphology based on morphologies of the cardiac waveforms.

2. The method of claim 1, wherein the atrial pacing is delivered at progressively higher rates.

3. The method of claim 1, wherein the atrial pacing is delivered in accordance with an automated atrial pacing pattern.

4. A method of discriminating between supraventricular and ventricular tachyarrhythmia, comprising:
   obtaining a plurality of cardiac templates from supraventricular cardiac waveforms and associating the plurality of cardiac templates with a plurality of cardiac rates to provide a plurality of rate-indexed templates;
   detecting a tachyarrhythmia episode of a patient;
   determining an episode cardiac rate for the detected tachyarrhythmia episode;
   identifying a closest cardiac rate from the plurality of cardiac rates that is closest to the episode cardiac rate;
   initially selecting from the plurality of rate-indexed templates an initial template associated with the closest cardiac rate;
   classifying the tachyarrhythmia episode as supraventricular tachyarrhythmia or ventricular tachyarrhythmia based on one or more templates selected from the plurality of rate-indexed templates, staffing with the initial template;
   creating supraventricular tachyarrhythmia by altering patient activity under controlled conditions;
   sensing cardiac waveforms during the created supraventricular tachyarrhythmia; and
   determining if the supraventricular rhythm exhibits rate dependent morphology based on the morphologies of the sensed cardiac waveforms.

5. A method of discriminating between supraventricular and ventricular tachyarrhythmia, comprising:
   obtaining a plurality of cardiac templates from supraventricular cardiac waveforms and associating the plurality of cardiac templates with a plurality of cardiac rates to provide a plurality of rate-indexed templates;
   detecting a tachyarrhythmia episode of a patient;
   determining an episode cardiac rate for the detected tachyarrhythmia episode;
   identifying a closest cardiac rate from the plurality of cardiac rates that is closest to the episode cardiac rate;
   initially selecting from the plurality of rate-indexed templates an initial template associated with the closest cardiac rate;
   classifying the tachyarrhythmia episode as supraventricular tachyarrhythmia or ventricular tachyarrhythmia based on one or more templates selected from the plurality of rate-indexed templates, staffing with the initial template;
   creating supraventricular tachyarrhythmia by administration of drugs to the patient;
   sensing cardiac waveforms during the created supraventricular tachyarrhythmia; and
   determining if the supraventricular rhythm exhibits rate dependent morphology based on morphologies of the sensed cardiac waveforms.

6. A method of discriminating between supraventricular and ventricular tachyarrhythmia, comprising:
   obtaining a plurality of cardiac templates from supraventricular cardiac waveforms and associating the plurality of cardiac templates with a plurality of cardiac rates to provide a plurality of rate-indexed templates;
   detecting a tachyarrhythmia episode of a patient;
   determining an episode cardiac rate for the detected tachyarrhythmia episode;
   identifying a closest cardiac rate from the plurality of cardiac rates that is closest to the episode cardiac rate;
   initially selecting from the plurality of rate-indexed templates an initial template associated with the closest cardiac rate;
   classifying the tachyarrhythmia episode as supraventricular tachyarrhythmia or ventricular tachyarrhythmia based on one or more templates selected from the plurality of rate-indexed templates, staffing with the initial template, the classifying being carried out by an implantable cardiac device; and
   determining one or more rates at which a change in morphology of the patient's supraventricular cardiac rhythm occurs.

7. A method of discriminating between supraventricular and ventricular tachyarrhythmia, comprising:
   obtaining a plurality of cardiac templates from supraventricular cardiac waveforms and associating the plurality of cardiac templates with a plurality of cardiac rates to provide a plurality of rate-indexed templates;
   detecting a tachyarrhythmia episode of a patient;
   determining an episode cardiac rate for the detected tachyarrhythmia episode;
   identifying a closest cardiac rate from the plurality of cardiac rates that is closest to the episode cardiac rate;
   initially selecting from the plurality of rate-indexed templates an initial template associated with the closest cardiac rate; and
   classifying the tachyarrhythmia episode based on one or more templates selected from the plurality of rate-indexed templates, staffing with the initial template, the classifying being carried out by an implantable cardiac device;
   wherein the obtaining comprises interpolating between at least two of the templates and forming the initial template based on the interpolation.

8. A medical system, comprising:
a lead system comprising cardiac electrodes configured to sense cardiac waveforms;
a template generator configured to form a plurality of rate-indexed templates characterizing cardiac waveforms sensed during supraventricular tachyarrhythmia, the rate-indexed templates comprising a plurality of cardiac templates associated with a plurality of cardiac rates;
an arrhythmia classification processor configured to detect a tachyarrhythmia episode and a corresponding cardiac rate from the sensed cardiac waveforms, the classification processor further being configured to:
  identify a closest cardiac rate from the plurality of cardiac rates that is closest to the detected cardiac rate;
  initially select from the plurality of rate-indexed templates an initial template associated with the closest cardiac rate; and
  classify the detected tachyarrhythmia episode using one or more templates selected from the plurality of rate-indexed templates, starting with the initial template;
a cardiac pacing circuit configured to create the supraventricular tachyarrhythmia through atrial pacing; and
a control system configured to determine if the supraventricular rhythm exhibits rate dependent morphology based on the cardiac waveforms sensed during the created supraventricular tachyarrhythmia and to form the plurality of rate-indexed templates using the cardiac waveforms sensed during the supraventricular tachyarrhythmia.

9. The medical system of claim 8, wherein the atrial pacing is delivered at progressively higher rates.

10. The medical system of claim 8, further comprising an automated atrial pacing pattern, and wherein the atrial pacing is delivered in accordance with the automated atrial pacing pattern.

11. A medical system, comprising:
means for forming rate indexed templates characterizing cardiac waveforms sensed during created supraventricular tachyarrhythmia, the rate-indexed templates comprising a plurality of cardiac templates associated with a plurality of cardiac rates;
means for detecting a tachyarrhythmia episode and a corresponding cardiac rate;
means for identifying a closest cardiac rate from the plurality of cardiac rates that is closest to the detected cardiac rate;
means for classifying the cardiac rhythms using selected ones of the rate indexed templates, starting with an initial template from the rate-indexed templates associated with the closest cardiac rate; and
means for creating the supraventricular tachyarrhythmia through atrial pacing.

12. A medical system, comprising:
means for forming rate indexed templates characterizing cardiac waveforms sensed during created supraventricular tachyarrhythmia, the rate-indexed templates comprising a plurality of cardiac templates associated with a plurality of cardiac rates;
means for detecting a tachyarrhythmia episode and a corresponding cardiac rate;
means for identifying a closest cardiac rate from the plurality of cardiac rates that is closest to the detected cardiac rate;
means for classifying the cardiac rhythms using selected ones of the rate indexed templates, starting with an initial template from the rate-indexed templates associated with the closest cardiac rate; and
means for determining if the rate-indexed templates exhibit rate dependent morphology between themselves.

* * * * *

UNITED STATES PATENT AND TRADEMARK OFFICE
CERTIFICATE OF CORRECTION

| | | |
|---|---|---|
| PATENT NO. | : 7,653,431 B2 | Page 1 of 1 |
| APPLICATION NO. | : 11/312280 | |
| DATED | : January 26, 2010 | |
| INVENTOR(S) | : Shelley Cazares et al. | |

It is certified that error appears in the above-identified patent and that said Letters Patent is hereby corrected as shown below:

Title page, item (*) Notice: should read as follows: Subject to any disclaimer, the term of this patent is extended or adjusted under 35 U.S.C. 154(b) by 934 days.

Signed and Sealed this

Fifteenth Day of June, 2010

David J. Kappos
*Director of the United States Patent and Trademark Office*